United States Patent [19]

Bradford et al.

[11] Patent Number: Plant 7,066

[45] Date of Patent: Dec. 5, 1989

[54] PEACH TREE (DIAMOND PRINCESS)

[76] Inventors: Norman G. Bradford, 11875 E. Savana Rd.; Lowell G. Bradford, 12439 E. Savana Rd., both of Le Grand, Calif. 95333

[21] Appl. No.: 294,103

[22] Filed: Jan. 6, 1989

[51] Int. Cl.[4] ..... A01H 5/00

[52] U.S. Cl. ..... Plt./43

[58] Field of Search ..... Plt./43

*Primary Examiner*—James R. Feyrer

[57] ABSTRACT

The present invention relates to a peach tree and more particularly to a new and distinct variety broadly characterized by a medium size, vigorous, hardy, very productive and regular bearing tree. The fruit matures under the ecological conditions described approximately the last week in June, with first picking on June 27, 1988, making it an early to mid-season ripening peach. The fruit is uniformly large in size, globose in shape, freestone in type, very firm in texture making excellent quality for keeping and shipping, almost full red in skin color at harvest time, and a delicious balance of acid and sugar in flavor. The variety was developed as a hybridized seedling from the selected seed parent, Red Diamond (U.S. Plant Pat. No. 3,165) nectarine, and an unnamed peach seedling as the selected pollen parent.

1 Drawing Sheet

BACKGROUND OF THE VARIETY

In a continuing effort to improve the quality of shipping fruits, we, the inventors, typically hybridize a large number of nectarine, peach, plum, apricot and cherry seedlings each year. The present invention relates to a new and distinct variety of peach tree, which has been denominated varietally as "Diamond Princess". The present variety was hybridized in 1984 by us in a cultivated area of our experimental orchard at Bradford Farms near Le Grand, Calif. in Merced County (San Joaquin Valley). It was the result of a seedling using Red Diamond (U.S. Plant Pat. No. 3,165) nectarine as the selected seed parent and an unnamed peach seedling as the selected pollen parent. Subsequent to origination of the present variety of peach tree, we asexually reproduced it by budding and grafting, and such reproduction of plant and fruit characteristics were true to the original plant in all respects.

The fruit produced by the present variety most nearly resembles the fruit of Redtop (not patented) by being a freestone peach that ripens in late June, but is distinguished therefrom an an improvement thereon by having a more globose shape, by having almost full red skin color at ripening time and by being extremely firm in texture, making it more desirable to the long distant shipper.

The present variety exhibits desirable characteristics common to its selected seed parent, Red Diamond (U.S. Plant Pat. No. 3,165) nectarine, by producing heavy crops of fruit that are nearly full red in color at harvest time, freestone in type, and very firm in texture, and also that ripens in late June. It noticeably differs from the Red Diamond by being a peach instead of a nectarine and by having a large blossom instead of a small blossom.

DRAWING

The accompanying photograph shows the characteristics of the whole fruit in skin color and form, a characteristic fruit divided on its suture plane showing the flesh and pit cavity, a typical stone, and typical leaves.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of eating ripe on July 5, 1988. All major color code designations are by reference to the Inter-Society Color Council, National Bureau of Standards. Common color names are also used occasionally.

TREE

Size: Medium.
Vigor: Vigorous.
Growth: Spreading and dense.
Form: Vase formed.
Hardiness: Hardy.
Production: Very productive.
Bearing: Regular bearer.
Trunk:
- *Size.*—Medium.
- *Texture.*—Medium.
- *Bark color.*—Moderate brown [58. m.Br].
- *Lenticels.*—Numerous. Color: Light yellowish brown [76. 1.yBr]. Size: 1/16" to ¼, [1.588–6.35 mm.].

Branches:
- *Size.*—Medium.
- *Texture.*—Medium.
- *Color.*—1st year wood — Topside: Grayish red [19. gy.R]. 1st year wood — Underside: Brilliant yellow green [116. brill.YG]. Older wood: Deep yellowish brown [75. deep yBr].
- *Lenticels.*—Numerous, small.

Leaves:
- *Size.*—Large. Average Length: 6.25" [158.8 mm.]. Average Width: 1½" [38.1 mm.].
- *Thickness.*—Medium.
- *Form.*—Elliptical.
- *Apex.*—Acutely pointed.
- *Base.*—Acute.
- *Surface.*—Smooth.

*Color.*—Dorsal Surface: Dark yellowish green [137. d.yG]. Ventral Surface: Moderate yellow green [120. m.YG].

*Margin.*—Finely serrate.

*Venation.*—Pinnately net veined.

*Petiole.*—Average Length: ½" [12.7 mm.]. Average Thickness: 3/32" [2.381 mm.]. Color: Moderate yellow green [120. m.YG].

*Glands.*—Numbers: 2 to 6 per leaf. Position: Most alternately positioned on petiole and base of blade. Size: Medium. Form: Reniform. Color: Moderate yellow green [120. m.YG].

*Stipules.*—Numerous. Average Length: ¼" [6.35 mm.].

Flower buds:

*Hardiness.*—Hardy.

*Size.*—Medium.

*Length.*—Medium.

*Form.*—Free.

*Surface.*—Pubescent.

Flowers:

*Blooming period.*—Medium to late, as compared with other varieties.

*Size.*—Large.

*Color.*—Pale purplish pink [252. p.pPk].

FRUIT

Maturity when described: Eating ripe, July 5, 1988.

Date of first picking: June 28, 1988.

Date of last picking: July 7, 1988.

Size: Uniform, large.

*Average diameter axially.*—2⅝" [66.68 mm].

*Average traversely in suture plane.*—2⅞" [73.03 mm].

Form: Uniform, symmetrical, globose to slightly oblate with some slight compression at both the apex and base.

*Longitudinal section form.*—Round to slightly oblate.

*Transverse section through diameter.*—Round, with a slight hump at the suture.

Suture: An inconspicuous line extending from the base to slightly beyond the apex with a depression beyond the pistil point.

Ventral surface: Rounded along the suture.

Lips: A slight protrusion along the suture, slightly unequal.

Cavity: Flaring, elongated in the suture plane, suture showing on one side only.

Base: Cuneate and slightly truncate.

Apex: Short, some depressed within the suture.

Pistil point: Mostly oblique, short in length.

Stem: Medium.

*Average length.*—7/16" [11.11 mm.].

*Average width.*—3/16" [4.763 mm.].

Skin:

*Thickness.*—Medium.

*Texture.*—Medium.

*Tenacity.*—Tenacious to flesh.

*Tendency to crack.*—Slight.

*Color.*—Dark red [16. d.R] over a deep yellowish pink [27. deep yPk] background.

Down: Scant, short, does not roll up when rubbed.

Flesh:

*Color.*—Light yellow [86. 1.Y] with the riper fruits having some deep yellowish pink [27. deep yPk] streaking very close to the stone.

*Surface of the pit cavity.*—Covered with deep yellowish pink [27. deep yPk] fibers.

*Amygdalin.*—Moderate.

*Juice.*—Moderate, rich.

*Texture.*—Firm, fine, crisp.

*Fibers.*—Abundant, fine, tender.

*Ripens.*—Evenly.

*Flavor.*—A delicious balance of acid and sugar.

*Aroma.*—Pronounced.

*Eating quality.*—Best.

STONE

Type: Freestone.

Form: Oblong.

Base: Straight.

Apex: Acute with a sharp tip.

Sides: Unequal.

Surface: Irregularly furrowed throughout, pitted toward the base, and ridged generally closer to the apex.

Ridges: Rounded.

Color: Moderate yellowish brown [77. m.yBr] with some strong red [12. s.R] tinting along the ridges.

Pit wall: ¼" [6.35 mm.] thick.

Tendency to split: Very slight.

Kernel:

*Form.*—Elliptical.

*Taste.*—Bitter.

*Viable.*—Yes.

*Average width.*—½" [12.7 mm.].

*Average length.*—13/16" [20.64 mm.].

Pellicle color: Light yellow [86. 1.Y].

Amygdalin: Abundant.

USE

Market: Fresh and long distance shipping.

Keeping quality: Good to excellent.

Shipping quality: Good to excellent.

Resistance to insects: No unusual susceptibilities noted.

Resistance to diseases: No unusual susceptibilities noted.

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct early to mid-season ripening variety of freestone peach tree, substantially as illustrated and described, which most nearly resembles the Redtop (not patented) peach variety by producing fruit that is freestone in type and ripens in late June, but is distinguished from and an improvement on that variety by having fruit that is more fully red in color at harvest time, more globose in shape, and much firmer in texture, all valuable assets for commercial long distant shipping peach varieties.

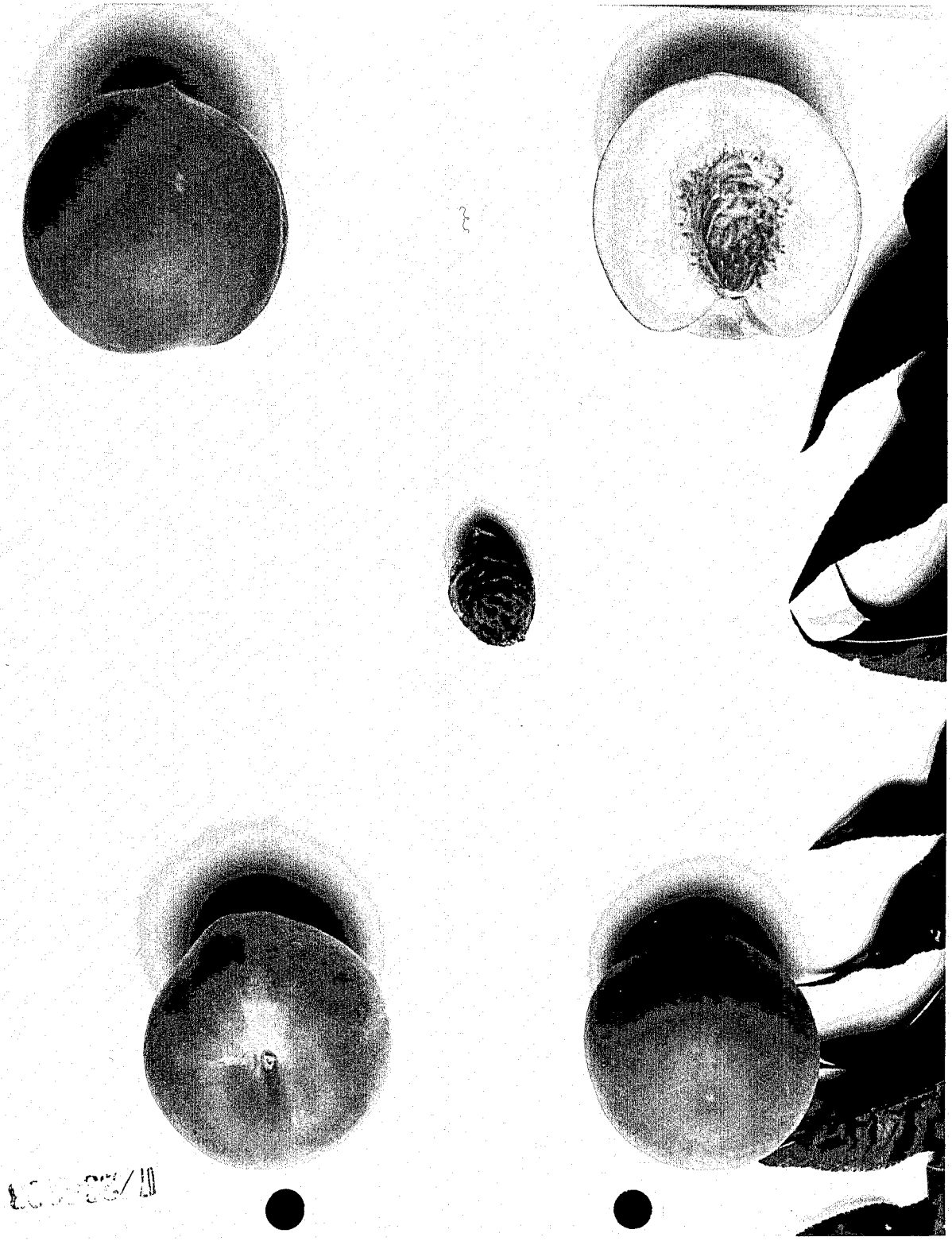

* * * * *